(12) United States Patent
Ambati et al.

(10) Patent No.: US 10,064,819 B2
(45) Date of Patent: *Sep. 4, 2018

(54) INTRAOCULAR DRUG DELIVERY DEVICE AND ASSOCIATED METHODS

(75) Inventors: Balamurali K. Ambati, Taylorsville, UT (US); Bruce K. Gale, Taylorsville, UT (US); Srinivas Rao Chennamaneni, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 997 days.

This patent is subject to a terminal disclaimer.

(21) Appl. No.: 13/543,597

(22) Filed: Jul. 6, 2012

(65) Prior Publication Data
US 2013/0302398 A1 Nov. 14, 2013

Related U.S. Application Data

(63) Continuation-in-part of application No. 13/211,169, filed on Aug. 16, 2011, which is a
(Continued)

(51) Int. Cl.
*A61M 31/00* (2006.01)
*A61K 9/00* (2006.01)
(Continued)

(52) U.S. Cl.
CPC .......... *A61K 9/0051* (2013.01); *A61K 9/2031* (2013.01); *A61K 31/573* (2013.01); *A61K 9/0017* (2013.01)

(58) Field of Classification Search
CPC ................... A61F 9/0017; A61F 2/16
(Continued)

(56) References Cited

U.S. PATENT DOCUMENTS

| 4,281,654 A | 8/1981 | Shell et al. |
| 4,762,496 A | 8/1988 | Maloney et al. |

(Continued)

FOREIGN PATENT DOCUMENTS

| CA | 2569375 A1 | 8/2006 |
| CA | 2513751 C | 1/2012 |

(Continued)

OTHER PUBLICATIONS

PCT Application PCT/US2009/043566; filed May 12, 2009; Balamurali K. Ambati; ISR dated Dec. 23, 2009.
(Continued)

*Primary Examiner* — Edelmira Bosques
(74) *Attorney, Agent, or Firm* — Thorpe North & Western, LLP

(57) ABSTRACT

Devices, systems, and methods for delivery of an active agent into the eye of a subject can include an intraocular active agent delivery device including an active agent dispersed within a biodegradable active agent matrix. The active agent includes dexamethasone and the delivery device is adapted to fit within a lens capsule or ciliary sulcus of an eye. The delivery device can be inserted into the lens capsule or ciliary sulcus of an eye during cataract surgery or for treatment of uveitis.

13 Claims, 7 Drawing Sheets

Related U.S. Application Data continuation-in-part of application No. 12/945,428, filed on Nov. 12, 2010, now Pat. No. 8,663,194, which is a continuation-in-part of application No. PCT/US2009/043566, filed on May 12, 2009.

(60) Provisional application No. 61/052,507, filed on May 12, 2008.

(51) Int. Cl.
*A61K 31/573* (2006.01)
*A61K 9/20* (2006.01)

(58) Field of Classification Search
USPC .................................. 604/521; 623/6.16
See application file for complete search history.

(56) References Cited

U.S. PATENT DOCUMENTS

| | | | |
|---|---|---|---|
| 5,098,443 A | 3/1992 | Parel et al. | |
| 5,183,662 A | 2/1993 | Morita et al. | |
| 5,185,152 A | 2/1993 | Peyman | |
| 5,275,624 A | 1/1994 | Hara et al. | |
| 5,330,768 A | 7/1994 | Park et al. | |
| 5,378,475 A | 1/1995 | Smith et al. | |
| 5,410,016 A | 4/1995 | Hubbell et al. | |
| 5,443,505 A | 8/1995 | Wong et al. | |
| 5,466,233 A | 11/1995 | Weiner et al. | |
| 5,518,730 A | 5/1996 | Fuisz | |
| 5,518,731 A | 5/1996 | Meadows | |
| 5,587,175 A | 12/1996 | Viegas et al. | |
| 5,620,699 A | 4/1997 | Meadows | |
| 5,626,863 A | 5/1997 | Hubbell et al. | |
| 5,660,851 A | 8/1997 | Domb | |
| 5,731,005 A | 3/1998 | Ottoboni et al. | |
| 5,766,242 A | 6/1998 | Wong et al. | |
| 5,807,581 A | 9/1998 | Rosenblatt et al. | |
| 5,824,072 A | 10/1998 | Wong | |
| 5,869,079 A | 2/1999 | Wong et al. | |
| 5,958,443 A | 9/1999 | Viegas et al. | |
| 6,004,573 A | 12/1999 | Rathi et al. | |
| 6,022,554 A | 2/2000 | Lee et al. | |
| 6,060,582 A | 5/2000 | Hubbell et al. | |
| 6,063,116 A | 5/2000 | Kelleher | |
| 6,063,396 A | 5/2000 | Kelleher | |
| 6,096,076 A | 8/2000 | Silvestrini | |
| 6,117,949 A | 9/2000 | Rathi et al. | |
| 6,214,044 B1 | 4/2001 | Silverstrini | |
| 6,217,895 B1 | 4/2001 | Guo et al. | |
| 6,217,896 B1 | 4/2001 | Benjamin | |
| 6,251,090 B1 | 6/2001 | Avery et al. | |
| 6,264,971 B1 | 7/2001 | Darougar et al. | |
| 6,277,413 B1* | 8/2001 | Sankaram | 424/501 |
| 6,309,669 B1 | 10/2001 | Setterstrom et al. | |
| 6,331,313 B1 | 12/2001 | Wong et al. | |
| 6,369,112 B1 | 4/2002 | Xia | |
| 6,369,116 B1 | 4/2002 | Wong et al. | |
| 6,416,777 B1 | 7/2002 | Yaacobi | |
| 6,548,078 B2 | 4/2003 | Guo et al. | |
| 6,627,600 B2 | 9/2003 | Boutignon | |
| 6,699,493 B2 | 3/2004 | Wong | |
| 6,713,081 B2 | 3/2004 | Robinson et al. | |
| 6,726,918 B1 | 4/2004 | Wong et al. | |
| 6,726,920 B1 | 4/2004 | Theeuwes et al. | |
| 6,756,049 B2 | 6/2004 | Brubaker et al. | |
| 7,033,605 B2 | 4/2006 | Wong | |
| 7,048,946 B1 | 5/2006 | Wong et al. | |
| 7,083,802 B2 | 8/2006 | Peyman | |
| 7,090,888 B2 | 8/2006 | Snyder et al. | |
| 7,186,789 B2 | 3/2007 | Hossainy et al. | |
| 7,195,774 B2 | 3/2007 | Carvalho et al. | |
| 7,455,855 B2 | 11/2008 | Kuwano et al. | |
| 7,527,621 B2 | 5/2009 | Greenberg | |
| 7,544,371 B2 | 6/2009 | Kunzler et al. | |
| 7,585,517 B2 | 9/2009 | Cooper et al. | |
| 7,589,057 B2 | 9/2009 | Chang et al. | |
| 7,625,582 B2 | 12/2009 | Wong | |
| 7,658,364 B2 | 2/2010 | Robinson et al. | |
| 7,749,530 B2 | 7/2010 | Spada et al. | |
| 7,767,223 B2 | 8/2010 | Wong | |
| 7,771,742 B2 | 8/2010 | Hughes et al. | |
| 7,799,336 B2 | 9/2010 | Hughes | |
| 7,846,468 B2 | 12/2010 | Wong | |
| 7,847,025 B2 | 12/2010 | Liu et al. | |
| 8,663,194 B2 | 3/2014 | Ambati et al. | |
| 2002/0039594 A1 | 4/2002 | Unger | |
| 2003/0149479 A1* | 8/2003 | Snyder et al. | 623/6.16 |
| 2004/0106906 A1 | 6/2004 | Yaacobi | |
| 2004/0126408 A1 | 7/2004 | Kabra et al. | |
| 2004/0137059 A1 | 7/2004 | Nivaggioli et al. | |
| 2004/0208909 A1 | 10/2004 | Brubaker et al. | |
| 2004/0253293 A1 | 12/2004 | Shafiee et al. | |
| 2005/0031669 A1 | 2/2005 | Shafiee et al. | |
| 2005/0048098 A1 | 3/2005 | Wong et al. | |
| 2005/0048099 A1 | 3/2005 | Shiah et al. | |
| 2005/0244458 A1 | 11/2005 | Huang et al. | |
| 2005/0244461 A1 | 11/2005 | Nivaggioli et al. | |
| 2005/0244462 A1 | 11/2005 | Farooq | |
| 2005/0244463 A1 | 11/2005 | Huang et al. | |
| 2005/0244465 A1 | 11/2005 | Nivaggioli et al. | |
| 2005/0244467 A1 | 11/2005 | Nivaggioli et al. | |
| 2005/0244468 A1 | 11/2005 | Huang et al. | |
| 2005/0244469 A1* | 11/2005 | Whitcup et al. | 424/427 |
| 2005/0244471 A1 | 11/2005 | Shiah et al. | |
| 2005/0244472 A1 | 11/2005 | Hughes et al. | |
| 2005/0244473 A1 | 11/2005 | Hughes et al. | |
| 2005/0244474 A1 | 11/2005 | Huang et al. | |
| 2005/0244476 A1 | 11/2005 | Burke et al. | |
| 2005/0244478 A1 | 11/2005 | Hughes et al. | |
| 2005/0244479 A1 | 11/2005 | Huang et al. | |
| 2005/0255144 A1 | 11/2005 | Schultz | |
| 2005/0271705 A1 | 12/2005 | Hughes et al. | |
| 2005/0281861 A1 | 12/2005 | Hughes et al. | |
| 2006/0008506 A1 | 1/2006 | Cipriano De Sousa et al. | |
| 2006/0051406 A1* | 3/2006 | Parmar | 424/450 |
| 2006/0067978 A1 | 3/2006 | Heiler et al. | |
| 2006/0078592 A1 | 4/2006 | Kunzler et al. | |
| 2006/0110429 A1 | 5/2006 | Reiff et al. | |
| 2006/0134174 A1 | 6/2006 | Bartels et al. | |
| 2006/0134175 A1 | 6/2006 | Bartels | |
| 2006/0134176 A1 | 6/2006 | Bartels | |
| 2006/0142706 A1* | 6/2006 | Roy et al. | 604/296 |
| 2006/0182781 A1 | 8/2006 | Hughes et al. | |
| 2006/0182783 A1 | 8/2006 | Hughes et al. | |
| 2006/0198871 A1 | 9/2006 | Wong | |
| 2006/0216328 A1 | 9/2006 | Kis et al. | |
| 2006/0233859 A1 | 10/2006 | Whitcup et al. | |
| 2006/0233860 A1 | 10/2006 | Chang et al. | |
| 2006/0257450 A1 | 11/2006 | Mudumba et al. | |
| 2006/0257452 A1 | 11/2006 | Hughes et al. | |
| 2006/0263409 A1 | 11/2006 | Peyman | |
| 2006/0292202 A1 | 12/2006 | Bartels | |
| 2006/0292203 A1 | 12/2006 | Dellamary et al. | |
| 2007/0059336 A1 | 3/2007 | Hughes et al. | |
| 2007/0123767 A1 | 5/2007 | Montegrande et al. | |
| 2007/0178138 A1 | 8/2007 | Pal et al. | |
| 2007/0212395 A1 | 9/2007 | Donello et al. | |
| 2007/0212397 A1 | 9/2007 | Roth | |
| 2007/0224247 A1 | 9/2007 | Chudzik et al. | |
| 2007/0280995 A1 | 12/2007 | Rabinovich-Guilatt et al. | |
| 2007/0281914 A1 | 12/2007 | Rabinovich-Guilatt et al. | |
| 2007/0298073 A1 | 12/2007 | Whitcup et al. | |
| 2007/0298074 A1 | 12/2007 | Robinson et al. | |
| 2007/0298076 A1 | 12/2007 | Wong | |
| 2008/0038316 A1 | 2/2008 | Wong et al. | |
| 2008/0038317 A1 | 2/2008 | Chang et al. | |
| 2008/0050420 A1 | 2/2008 | Wong | |
| 2008/0050421 A1 | 2/2008 | Wong | |
| 2008/0057101 A1 | 3/2008 | Roorda | |
| 2008/0057102 A1 | 3/2008 | Roorda | |
| 2008/0057103 A1 | 3/2008 | Roorda | |
| 2008/0063687 A1 | 3/2008 | Chou et al. | |
| 2008/0069859 A1 | 3/2008 | Wong | |
| 2008/0107712 A1 | 5/2008 | Shiah et al. | |

(56) References Cited

U.S. PATENT DOCUMENTS

| | | |
|---|---|---|
| 2008/0124376 A1 | 5/2008 | Pruitt et al. |
| 2008/0145403 A1 | 6/2008 | Spada et al. |
| 2008/0145405 A1 | 6/2008 | Kunzler et al. |
| 2008/0145406 A1 | 6/2008 | Asgharian |
| 2008/0147021 A1 | 6/2008 | Jani |
| 2008/0152694 A1 | 6/2008 | Lobl |
| 2008/0131481 A1 | 7/2008 | Hughes |
| 2008/0131484 A1 | 7/2008 | Robinson et al. |
| 2008/0167600 A1 | 7/2008 | Peyman |
| 2008/0172014 A1 | 7/2008 | Whitcup et al. |
| 2008/0181929 A1 | 7/2008 | Robinson et al. |
| 2008/0200860 A1 | 8/2008 | Tu et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0268021 A1 | 10/2008 | Warren et al. |
| 2008/0269119 A1 | 10/2008 | Griffith et al. |
| 2008/0286334 A1 | 11/2008 | Shiah et al. |
| 2008/0286336 A1 | 11/2008 | Shiah et al. |
| 2008/0292679 A1 | 11/2008 | Lyons et al. |
| 2009/0093780 A1 | 4/2009 | Tuitupou et al. |
| 2009/0130176 A1 | 5/2009 | Bossy-Nobs et al. |
| 2009/0148498 A1 | 6/2009 | Libin et al. |
| 2009/0148499 A1 | 6/2009 | Wong et al. |
| 2009/0162417 A1 | 6/2009 | Eells |
| 2009/0196905 A1 | 8/2009 | Spada et al. |
| 2009/0196906 A1 | 8/2009 | Spada et al. |
| 2009/0214619 A1 | 8/2009 | Reiff et al. |
| 2009/0220572 A1 | 9/2009 | Deschatelets et al. |
| 2009/0258924 A1 | 10/2009 | Lyons et al. |
| 2009/0274744 A1 | 11/2009 | Kunzler et al. |
| 2009/0274745 A1 | 11/2009 | Kunzler et al. |
| 2009/0286773 A1 | 11/2009 | Spada et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2010/0119519 A1 | 5/2010 | Peyman |
| 2010/0158980 A1 | 6/2010 | Kopezynski et al. |
| 2010/0189766 A1 | 7/2010 | Utkhede et al. |
| 2010/0209478 A1 | 8/2010 | Sawhney et al. |
| 2010/0215720 A1 | 8/2010 | Garagorri Ganchegui et al. |
| 2010/0247606 A1 | 9/2010 | Robinson et al. |
| 2010/0255061 A1 | 10/2010 | De Juan, Jr. et al. |
| 2010/0311808 A1 | 12/2010 | Lyons et al. |
| 2011/0230963 A1 | 9/2011 | Cuevas |
| 2011/0282328 A1 | 11/2011 | Ambati et al. |
| 2013/0302398 A1 | 11/2013 | Ambati et al. |

FOREIGN PATENT DOCUMENTS

| | | |
|---|---|---|
| JP | S62-201816 A | 5/1987 |
| JP | H11506450 A | 6/1999 |
| JP | 2004210798 A | 7/2004 |
| JP | 2007217699 A | 8/2007 |
| JP | 2007535535 A | 12/2007 |
| JP | 2008523131 A | 7/2008 |
| JP | 2009508646 A | 3/2009 |
| WO | WO 95/17900 A1 | 7/1995 |
| WO | WO 02/055258058 | 7/2002 |
| WO | WO 2007/035473 | 3/2007 |
| WO | WO 2007/112946 | 10/2007 |
| WO | WO 2007/121485 | 10/2007 |
| WO | WO 2008/011125 | 1/2008 |
| WO | WO 2008025111 A2 | 3/2008 |
| WO | WO 2009/140246 | 11/2009 |

OTHER PUBLICATIONS

Ram et al.; "Phacoemulsification and intraocular lens implantation after inadvertent intracapsular injection of intravitreal dexamethasone implant"; BMJ Case Reports; (Dec. 12, 2012); 3 pages; <doi: 10.1136/bcr-2012-007494 >.

Vianna et al.; "Intracapsular dexamethasone implant in patients undergoing phacoemulsification and intraocular lens implantation"; Arquivos Brasileiros de Oftalmologia; (2013); pp. 226-228; vol. 76, No. 4.

Garg et al.; "Cystoid Macular Edema"; Cystoid Macular Edema—EyeWiki; (Jan. 26, 2014); 6 pages; [retrieved on Feb. 25, 2018] Retrieved online from [<URL: https://web.archive.org/web/20140126073222/http://evewiki.aao.org/Cystoid_Macular_Edema >].

Normal Polymer; "Normal"; Normal Polymer—Poly(DL lactide-co-glycolide; (Jan. 31, 2016); 3 pages; [retrieved on Feb. 23, 2018] Retrieved online from [<URL: https://web.archive.org/web/20160131164109/http://normalpolymer.com/poly-DL-lactide-co-glycolide.php >].

International Search Report dated Apr. 6, 2018, in International Application No. PCT/US17/68571, filed Dec. 27, 2017; 2 pages.

* cited by examiner

INTRAOCULAR DRUG DELIVERY DEVICE AND ASSOCIATED METHODS

RELATED APPLICATIONS

This application is a continuation-in-part of U.S. application Ser. No. 13/211,169, filed Aug. 16, 2011, which is a continuation-in-part of U.S. application Ser. No. 12/945,428, filed Nov. 12, 2010, which is a continuation-in-part of International Application No. PCT/US2009/043566, filed May 12, 2009, which claims priority to U.S. Provisional Application No. 61/052,507, filed May 12, 2008, which are each incorporated herein by reference.

FIELD OF THE INVENTION

The present invention relates to systems, methods, and devices for the sustained and targeted (local) delivery of a pharmaceutical active agent into a subject's eye. Accordingly, the present invention involves the fields of polymer chemistry, material science, polymer science, drug delivery, formulation science, pharmaceutical sciences, and medicine, particularly ophthalmology.

BACKGROUND

Age-related macular degeneration (AMD) and glaucoma are two of the leading causes of blindness in the United States and across the world. Present glaucoma therapies generally require polypharmacy, where subjects are often prescribed several topical agents that must be applied to the eye with varying frequencies, in some cases up to 3 or 4 times a day. These dosing regimens are often difficult for subjects to consistently follow, and many individuals progress to needing surgical treatments such as intraocular shunts or trabeculectomies, which have significant attendant complications.

Subjects having macular degeneration are often required to have monthly intravitreal injections. Such injections are painful and may lead to retinal detachment, endophthalmitis, and other complications. Furthermore, these injections are generally performed only by retinal surgeons, a small fraction of the ophthalmic community, producing a bottleneck in eye care delivery and increased expense.

Postoperative surgery inflammation is associated with raise intraocular pressure (IOP), and increase the likelihood of cystoid macular edema (CME), synechial formation, posterior capsule opacification (PCO), and secondary glaucoma. Patient compliance is of concern in the management of postoperative inflammation because multiple eye drops must be taken multiple times per day at regular intervals over the course of weeks. Poor compliance compromises the efficacy of topical drugs, which are further limited by corneal absorption and have highly variable intraocular concentrations during the therapeutic course. Uveitis specifically refers to inflammation of the middle layer of the eye, termed the "uvea" but in common usage may refer to any inflammatory process involving the interior of the eye. Uveitis is estimated to be responsible for approximately 10% of the blindness in the United States.

Postoperative cataract surgery inflammation can be well controlled by improving patient compliance. Available literature and experience shows penetration of the drug after topical administration is poor and higher systemic concentration means frequent systemic adverse events. All of these factors highlight the need for sustained intraocular delivery for pharmaceutical active agents to effectively control inflammation.

Figure 1:
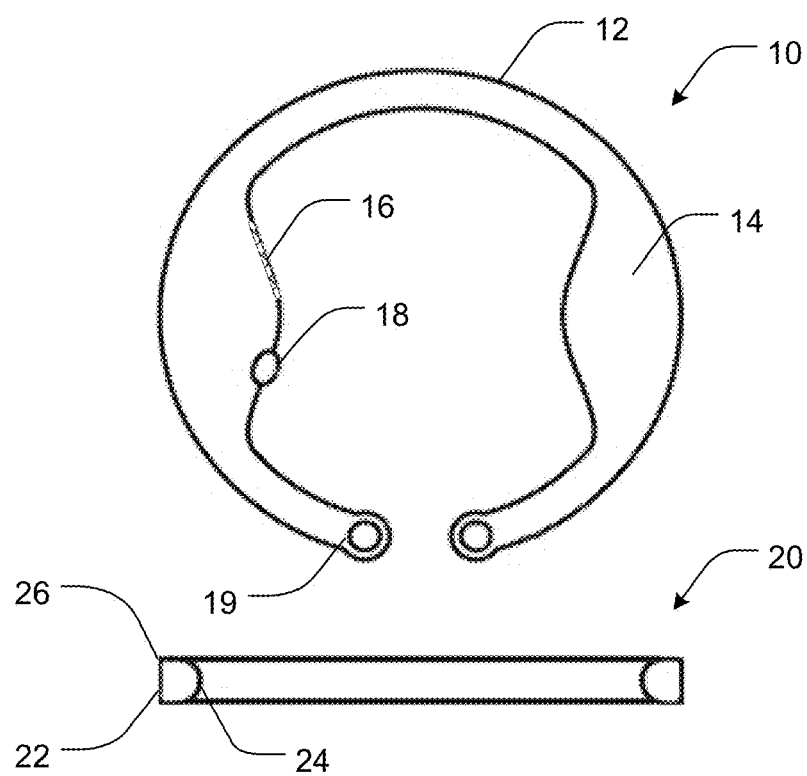
FIG. 1 is a top view of an active agent delivery device showing dedicated valve and membrane locations.

These drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations.

DETAILED DESCRIPTION OF THE INVENTION

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

It must be noted that, as used in this specification and the appended claims, the singular forms "a," "an," and "the" include plural referents unless the context clearly dictates otherwise. Thus, for example, reference to "a drug" includes reference to one or more of such drugs, "an excipient" includes reference to one or more of such excipients, and "filling" refers to one or more of such steps.

Definitions

In describing and claiming the present invention, the following terminology will be used in accordance with the definitions set forth below.

As used herein, "active agent," "bioactive agent," "pharmaceutically active agent," and "drug," may be used interchangeably to refer to an agent or substance that has measurable specified or selected physiologic activity when administered to a subject in a significant or effective amount. These terms of art are well-known in the pharmaceutical and medicinal arts.

As used herein, "formulation" and "composition" may be used interchangeably herein, and refer to a combination of two or more elements, or substances. In some embodiments a composition can include an active agent, an excipient, or a carrier to enhance delivery, depot formation, etc.

As used herein, "subject" refers to a mammal that may benefit from the administration of a composition or method as recited herein. Examples of subjects include humans, and can also include other animals such as horses, pigs, cattle, dogs, cats, rabbits, aquatic mammals, etc.

As used herein, the terms "reservoir" and "active agent reservoir" may be used interchangeably, and refer to a body, a mass, or a cavity that can contain an active agent. As such, a reservoir can include any structure that may contain a liquid, a gelatin, a sponge, a semi-solid, a solid or any other form of active agent known to one of ordinary skill in the art. In some aspects a reservoir can also contain an active agent matrix. Such matrixes are well known in the art.

As used herein, the term "intraocular lens" refers to a lens that is utilized to replace a lens in the eye of a subject. Such intraocular lenses can be synthetic or biological in nature. Furthermore, in some aspects the term "intraocular lens" can also refer to the original natural lens that is associated with the eye.

As used herein, the term "annular housing" can be used to describe a housing of a circular or semicircular nature. Thus an annular housing can be substantially annular, fully annular, fully circular, oval, partially circular, c-shaped, D-shaped, etc. In the present invention, typically the cross-section is also annular.

As used herein, the term "ciliary sulcus" refers to the space between the posterior root of the iris and the ciliary body of the eye.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the relevant effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

Any steps recited in any method or process claims may be executed in any order and are not limited to the order presented in the claims unless otherwise stated. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Intraocular Drug Delivery Device

An intraocular drug delivery device can provide improved ophthalmic drug delivery by alleviating the need for multiple injections or complex eyedrop regimens by providing an intra-capsular reservoir which is implantable and biodegrades such that subsequent surgery is often unnecessary. Further, the device can deliver a variety or combination of different medicines.

A novel intraocular drug delivery device, system, and associated methods for providing sustained release of ocular active agents for extended periods of time are disclosed and described. One problem with many eye diseases such as Age-related Macular Degeneration (AMD) is the constant need for a subject to receive painful ocular injections, which have significant risks of retinal detachment, vitreous hemorrhage, and endophthalmitis. The intraocular drug delivery device allows for sustained release of an active agent over time, thus eliminating the need for frequent ocular injections. Additionally, the intraocular drug delivery device can be refillable, thus reducing the frequency of invasive ocular procedures for subjects having disorders such as AMD. Depending on the active agent being used and the configuration of the device, the time between refilling procedures can be extended to every 3 months, 6 months, a year or more.

In some aspects, the device can be implantable during cataract surgery, essentially "piggybacking" on the cataract extraction, and thus eliminating the need for additional surgical procedures. One benefit to "piggybacking" on the cataract extraction is the ability to deliver steroids, antibiotics, and various non-steroidal agents directly to the eye after surgery, thus helping to minimize complications such as cystoid macular edema. An annular housing can improve lens capsule stability in subjects having unstable capsules and prevent posterior capsule opacification and capsular fibrosis by inhibiting lens epithelial cell migration from the anterior to posterior capsule.

An injection to fill or refill the device can be accomplished through existing cataract surgical incisions for those subjects that received the device during a cataract surgery. Such a refilling procedure may thus reduce the level of pain and risk experienced by a subject as compared to traditional intravitreal injections. In other aspects, the device can be implanted in a surgery that is separate from a cataract procedure, e.g., subsequent to a previous cataract extraction with reopening of the lens capsule.

It should be noted that neovascularization is a key pathobiological process in a variety of eye diseases, such as AMD, proliferative diabetic retinopathy, vascular occlusive disease, and radiation retinopathy. Additionally, the incidence of glaucoma is increasing worldwide. Many other disorders, including severe uveitis and geographic atrophy in AMD, can be treated using such an intraocular drug delivery device. Such a refillable, generally sutureless, anterior segment drug delivery device thus has great potential to improve the quality of life for subjects.

The drug delivery device can continuously deliver dexamethasone or other anti-inflammatory agents with near zero order kinetics for up to two weeks. Treatment of uveitis needs long term (6-8 weeks) sustained delivery of anti-inflammatory agents. The biggest disadvantage with topical drops is negligible concentrations of drugs will reach the posterior segment of the eye and especially the retina/choroid. The designed and disclosed drug delivery device can deliver dexamethasone continuously with near zero order kinetics both to the anterior and posterior chamber thus effectively controlling the inflammation.

Therefore, the opportunity exists to improve management of AMD, postoperative surgery inflammation and uveitis patients undergoing cataract surgery by sustained release of pharmaceutical active agent(s). Accordingly, the present invention provides systems, devices, and associated methods for the delivery of active agents into the eye of a subject. In one aspect, as is shown in FIG. 1, an ocular active agent delivery device 10 can include an active agent reservoir 14 disposed in an annular housing 12. The annular housing 12 can be sized and designed to fit inside of a lens capsule and at least partially encircle (but not obstruct) a line of sight of an intraocular lens within the lens capsule. In one aspect, the intraocular device can be sutureless. A sutureless device can be defined as a device or structure that can be inserted and retained within a lens capsule without the need for a suture to hold the device in place.

The device can further include a semipermeable membrane 16 operatively coupled to the active agent reservoir 14, where the semipermeable membrane 16 is configured to allow diffusion of an active agent from the active agent reservoir 14. Additionally, a valve 18 can be operatively coupled to the active agent reservoir 14 such as along a wall thereof. The valve 18 can be oriented, sized and designed to allow filling of the active agent reservoir 14 with an active agent. The reservoir or shell of the device can be rigid or inflatable and flexible In one specific aspect the active agent reservoir contains at least one active agent. In another aspect the active agent reservoir contains an active agent matrix. Furthermore, manipulation handles 19 such as eyelets or hooks can be optionally included in the housing to facilitate manipulation and placement of the delivery device.

In one aspect, the intraocular device can additionally include a radio frequency transducer battery source coupled to a biosensor. Biosensors can include pressure or molecular biosensors. Such a biosensor can be used to detect intraocular levels of analytes such as glucose, VEGF, disease biomarkers, and delivered active agent to name a few. The biosensor can also be used to detect and monitor intraocular pressure using a pressure transducer. One example of such a pressure sensor transducer is a flexible structure that changes volume in response to changes in intraocular pressure. The transducer can include a parallel plate capacitor and a discrete inductor connected in series to form an L-C circuit. As pressure surrounding the plates changes, separation of the capacitor plates also changes which affects the resonant frequency of the L-C circuit. Other transducers can also be used.

The active agent delivery devices can optionally contain additional/separated reservoirs for the delivery of additional active agents or other desired therapeutically beneficial substances. In one aspect, for example, the device can include at least one secondary active agent reservoir disposed within the annular housing. Corresponding refill valves can also be added for each reservoir. In one specific aspect, the at least one secondary active agent reservoir contains at least one active agent. It should be noted that the secondary active agent reservoir can contain an active agent that is the same or different from the active agent contained in the active agent reservoir. Individual reservoirs can be segregated by impermeable walls or merely by providing an adjacent drug matrix. Furthermore, in one optional aspect the device can include an osmotic pump operatively coupled to the active agent reservoir, where the osmotic pump is configured to facilitate delivery of an active agent from the active agent reservoir.

Numerous physical configurations for the annular housing can be suitable. In one aspect, for example, the annular housing 12 can form an incomplete circle such as a C-shape, as is shown in FIG. 1, a half circle or other arcuate shape. In another aspect, as is shown in the cross-section 20 of the annular housing 12, the annular housing can have an outer circumferential surface 22 and an inner circumferential surface 24, where the outer circumferential surface 22 is substantially squared 26. Such squaring of the outer circumferential surface can be beneficial in reducing the incidence of capsular fibrosis, although other shapes can also be suitable such as circular. Agents can optionally be coated on the annular housing to reduce the incidence of capsular fibrosis. Non-limiting examples of such agents include anticell proliferative agents, anti-TGF-beta agents, a5b1 integrin antagonists, rapamycin, and the like.

Various materials are contemplated for use as the annular housing that can securely hold the various components of the device. It can be additionally beneficial to utilize materials that provide some level of flexibility to avoid damage or irritation to the eye surface. Any material having properties beneficial to the construction of such a device would be considered to be within the scope of the present invention. For example, the housing material can include, without limitation, plastics or polymers such as Teflon, nylons, polyesters, polyimides, polyurethanes, polyethylenes, polycarbonates, silicone, polymethylmethacrylate, acrylic polymers, polypropylene, metals such as titanium, composites, etc.

Additionally, semipermeable membranes are well known in the art, and numerous materials can be suitable for use depending on the nature of the annular housing material and the active agent(s) being used. In one aspect, however, the semipermeable membrane can include materials such as, but without limitation, polyvinyl alcohols, ethylvinyl alcohols, cellulose esters, polypropylenes, and other semipermeable materials that exhibit ocular biocompatibility. In one specific aspect, the semipermeable membrane can be a cellulose ester. Additionally, the semipermeable membranes can be hydrophilic or amphiphilic or hydrophobic. In one specific aspect, the semipermeable membrane can be hydrophilic.

The pore size of a semipermeable membrane can vary depending on the semipermeable membrane material, active agent being utilized, and the desired permeability kinetics. In one aspect, for example, the pore size can be from about 5 nm to about 200 nm. In another aspect, the pore size can be from about 10 nm to about 100 nm. In yet another aspect, the pore size can be from about 10 nm to about 40 nm. In a further aspect, the pore size can be from about 20 nm to about 100 nm. In yet a further aspect, the pore size can be from about 20 nm to about 30 nm, and in one specific aspect the pore size can be about 25 nm. Further, larger pores of 100 nm to 10 microns can also be made. Such pores can be formed, for example, using lasers.

Figure 2:
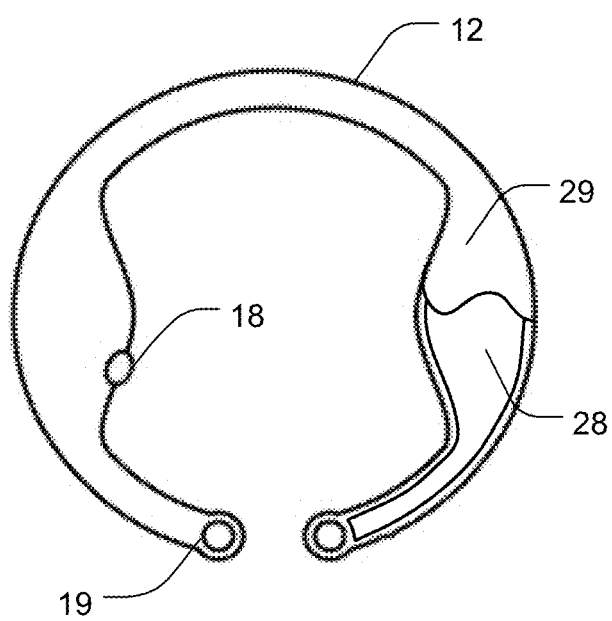
FIG. 2 is a top partial cut-away view of an active agent delivery device in accordance with another aspect of the present invention.

The semipermeable membrane can be formed and designed for a given use. For example, the pore size and exposed surface area over which the membrane covers the housing can be varied based on desired rates of delivery, active agent size, and other factors. In one aspect, the semipermeable membrane can be a "window" portion of the device housing as is shown in FIG. 1 (16) as a distinct portion of the annular housing. In another aspect, the semipermeable membrane can be a structural surface of the device such as a floor, wall, ceiling, or portion thereof, or laminated within the structure of the device. In one aspect, as is shown in FIG. 2, the active agent reservoir 28 can be an interior portion of the device and the semipermeable membrane 29 can be a "ceiling" or covering over a the active agent reservoir. In some cases, as is shown in FIG. 2, the semipermeable membrane can comprise an entire surface of the intraocular device. In one alternative embodiment, the annular housing can be entirely or substantially entirely the semipermeable membrane. Furthermore, in order to provide a more even distribution of active agent to the eye, semipermeable membrane materials can be used for a plurality of locations around the annular housing or as the primary construction of the annular housing. Optional mesh material can be layered on an exterior surface of the annular housing. In yet another optional embodiment, the annular housing can be coated with a protective coating, e.g. polyethylene glycol or the like. The protective coating can increase biocompatibility, reduce capsular fibrosis, and/or otherwise alter device performance.

As has been described, in one aspect the reservoir can contain the active agent in the active agent reservoir in a substantially liquid or viscous form. In another aspect, the active agent can reside in a drug matrix within the active agent reservoir. Drug matrixes are well known in the art, and can include a variety of polymeric and non-polymeric materials. Specific non-limiting examples of suitable matrix materials include biodegradable polymers (e.g. PLGA, albumin), colloidal suspensions, nanoparticles, microparticles, microspheres, nanospheres, hydrogels, purites, polycarbophil, solid matrix, and the like.

Additionally, the active agent can be included in the reservoir in any form, including, without limitation, a liquid, a sponge, a gelatinous, a semi-solid, or a solid form. Although numerous active agents are known for the treatment of various eye conditions, a few examples used in the treatment or prophylaxis of eye diseases such as AMD (neovascular form or atrophic form), glaucoma, diabetic retinopathy, Retinopathy of Prematurity, uveitis, corneal transplant rejection, capsular fibrosis, posterior capsule opacification, retinal vein occlusions, infections, and the like, can be treated with non-limiting active agents such as dexamethasone, bevacizumab (Avastin®), Timolol, Latanoprost, Brimonidine, Nepafenac, and ranibizumab (Lucentis®). Other non-limiting examples of active agents include antibiotics, prednisolone, fluocinolide, and the like. Treatment regimens can additionally include anti-VEGF aptamers such as pegaptanib (Macugen®), anti-VEGF Fab fragments such as ranibizumab (Lucentis®), integrin antagonists, various photodynamic therapies, and the like.

A variety of valve devices are contemplated and any such material or device that allows filling of a drug reservoir while also preventing undesirable egress of material through the valve should be considered to be within the present scope. Generally, the valve can be located at a dedicated valve location or may be the annular housing. For example, the valve can be configured as a slit in a membrane that functions to contain the active agent within the reservoir while allowing a needle to be inserted through the slit. In another aspect, the valve can be an elastomeric material that allows access of a needle and reseals once the needle is withdrawn, e.g. silicone elastomer or polyurethane rubber. In this embodiment, the device can be entirely made of an elastomeric material such that the annular housing also serves as the valve. The location of filling can then be chosen by considerations of convenience regardless of the orientation of the device and/or patient. Further, this option can be particularly desirable for single use bioerodible configurations. In such cases, the drug reservoir can be filled during manufacture, before insertion or after insertion. Alternatively, the elastomeric material can form a portion of the annular housing surface as with other valve options described herein. In yet another aspect, the valve can be a one-way tricuspid valve that allows a reservoir to be easily refilled. In a further aspect, the valve can be a hinged valve. Such passive microvalves can be beneficial in easing manufacturing complications and provide sufficient barrier to loss of materials from within the reservoir. In yet another aspect, the valve can incorporate a hinged door design to allow access for filling the reservoir. Furthermore, the valve can be of a variety of sizes, depending on the intended use and configuration of a filling apparatus, such as a needle or a cannula. In one aspect, the valve diameter can be about 0.016 inches to allow access of a standard ophthalmic cannula. The valve can incorporate a docking system to enable capture and stabilization of the device by a cannulation system immediately prior to filling or refilling.

There are several optional embodiments for manufacture of the delivery system. As previously mentioned, the semipermeable membrane can also serve as the housing. The valve can be placed in the interior of the device and bonded, molded and/or melted to the membrane in a desired location. If the semipermeable membrane is not the housing, the valve can be attached to either the semipermeable membrane or the housing chemical and/or photoactivated bonding, molding, lamination, and/or melting. Bonding can include a biocompatible adhesive or a chemical activation step to encourage covalent attachment between the components. The semipermeable membrane can be placed in windows of the housing and bonded, melted and/or molded to the housing. The housing can be created either by molding it around a preformed structure (such as a wire), or by creating two mirror-image half structures (such as a sandwich structure) and then bonding them together to form a hollow interior structure. Techniques such computer controlled knife plotters, hot embossing, laser ablation, soft lithography, injection molding, and the like can be used to form a suitable mold and/or the housing. One optional manufacturing method is a PDMS tape method which involves cutting PDMS coated double-sided tape with a knife plotter. The membrane can be integrated and sealed to the housing any number of techniques including, but not limited to, glue or clamping with microstereo lithography, electrochemical wet etching, deep reactive ion etching, ion beam lithography, and the like.

Figure 3:
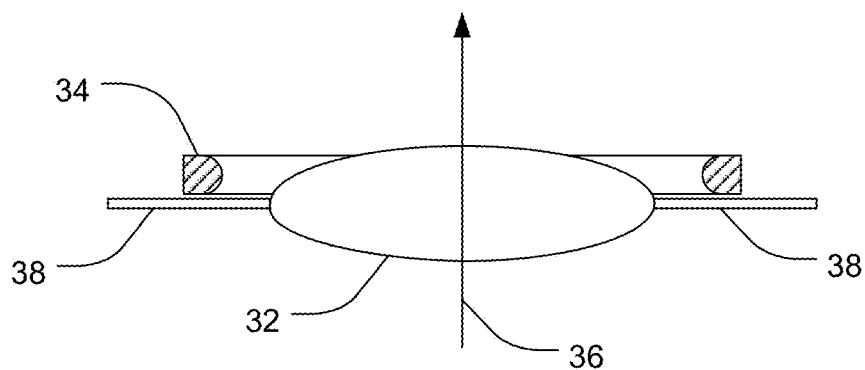
FIG. 3 is a cross-sectional view of an active agent delivery device in accordance with yet another aspect of the present invention.

Another aspect of the present invention provides a system for delivering an active agent into an eye of a subject. As is shown in FIG. 3, such a system can include an intraocular lens 32 and an active agent delivery device 34. The active agent delivery device can include an active agent reservoir disposed in an annular housing, where the annular housing at least partially encircles a line of sight 36 of the intraocular lens, and a semipermeable membrane operatively coupled to the active agent reservoir, where the semipermeable membrane is configured to allow diffusion of an active agent from the active agent reservoir. Note that the active agent reservoir is not shown in FIG. 3 for clarity. The device can further include a valve operatively coupled to the active agent reservoir, where the valve is configured to allow filling of the active agent reservoir. FIG. 3 additionally shows an attachment structure 38 that is used to affix the lens 32 into the eye. It should be noted that the placement of the active agent delivery device in FIG. 3 is merely exemplary, and as such alternative placements would be considered to be within the present scope provided that the line of sight is substantially unobstructed. For example, rather than being placed superior to the lens as is shown in FIG. 3, the active agent delivery device can be located inferior to the lens (not shown).

Yet another aspect of the present invention provides a method of delivering an active agent into an eye of a subject. Such a method can include performing a cataract removal surgery on the eye of the subject, further including removing an existing lens from the eye of the subject, inserting an intraocular lens into the eye of the subject, and associating a device as described herein with the intraocular lens such that the annular housing at least partially encircles a line of sight of the intraocular lens. The delivery device may be attached or detached from an intraocular lens. The delivery device can be associated by actual contact or sufficient proximity to allow effective diffusion of active agent to target areas of the eye. The delivery device can itself be a biodegradable matrix or a reservoir system. A biodegradable system would have value in routine cataract surgery to enable short-term/time-limited delivery of postoperative medicines which would other require eyedrop usage by the patient. The lens that is removed can be the original natural lens of the eye, or it can be a lens that was previously inserted into the eye as a result of a prior procedure.

Numerous methods of associating the device into the eye are contemplated. For example, in one aspect, the annular housing can be associated with the intraocular lens prior to inserting the intraocular lens into the eye. In such cases it would be necessary to configure the annular housing to comply with any requirements of the surgical procedure. For example, cataract surgeries are often performed through a small incision. One standard size incision is about 2.75 mm; although this device can be compatible with smaller or larger incision sizes as well. As such, the intraocular lens assembly can be shaped to allow insertion through this small opening. Thus the active agent delivery device must also be configured to be inserted with the intraocular lens assembly, e.g. by shape and choice of resilient and flexible material for the housing. Additionally, the active agent delivery device can also be physically coupled or decoupled to the intraocular lens assembly prior to insertion of the assembly into the eye. In another aspect, the annular housing can be associated with the intraocular lens assembly following insertion of the lens into the eye. The capsular bag can be readily reopened for a patient having prior cataract surgery. Thus, the insertion of the delivery device can be performed immediately prior to insertion of an intraocular lens or later in time as a separate procedure.

In another aspect, the method can further include orienting the valve with respect to the eye to allow external access for filling the active agent reservoir. The active agent reservoir can be filled prior to insertion into the eye, or the reservoir can be filled following insertion into the eye. Regarding the initial insertion, certain configurations of annular housings can preclude inserting an annular housing having a filled reservoir into the eye due to folding limitations associated with a full active agent reservoir. In such circumstances, it can be beneficial to fill the reservoir following insertion into the eye. Additionally, a depleted active agent reservoir can be refilled through the valve for reuse of the device. As such, it can be beneficial to orient the valve into a configuration that allows easy access for filling. In particular, the devices of the present invention can allow for refilling via through an edge of the cornea anterior segment of the eye rather than via the vitreous or posterior segment of the eye. Depending on the size of the reservoir and the nature of the active agent, an active agent delivery device can deliver a drug for up to 6 months or up to a year before refilling is required. The specific delivery rate and time can be affected by the size of the reservoir, the type of membrane, choice of drug matrix, and/or a variety of other factors. Refill cannulas and/or pre-packaged drug-matrix-reservoir materials can also be prepared to compliment extended use of the inserted delivery device.

In another aspect, the device may be rigid or inflatable, i.e., the device can be collapsed prior to insertion into the lens capsule and then inflated with the drug matrix in situ.

Consistent with the principles set forth above, another optional configuration includes the use of a homogeneous delivery device formed of an active agent matrix and the active agent. The ocular active agent delivery device can be configured to fit within a lens capsule or ciliary sulcus of an eye. The delivery device can be shaped in any geometry which allows for insertion into the lens capsule or ciliary sulcus. In one aspect, the delivery device can be shaped as an annular body being configured to at least partially encircle a line of sight of an intraocular lens within the lens capsule. Such annular bodies can be shaped as an incomplete circle, a semi-circle, or an arcuate segment. FIG. 1 illustrates an incomplete circle, while a semi-circle and arcuate segment shape would be segmented versions of this configuration. A semi-circle and arcuate segments can allow for insertion along outer edges of the lens capsule or within the ciliary sulcus such that the device is contoured to fit in these areas without applying excessive pressure to associated tissue. The annular body is configured to fit inside of a lens capsule and at least partially encircling a line of sight of an intraocular lens within the lens capsule. Typically, this configuration is a C-shape although a more modest arcuate profile can be used (i.e. a 10° to 110° arcuate profile, although up to about 350° can be suitable). In one aspect, the annular body is formed of an active agent matrix having the active agent dispersed therein. Thus, the active agent matrix is capable of functioning as a semipermeable membrane to allow diffusion of the active agent from the active agent matrix. The active agent can diffuse through the annular body forming a unitary and homogeneous device. In such cases the active agent matrix can also function as a valve to allow filling of the active agent reservoir with the active agent. However, other suitable shapes can include, but are not limited to, discs, pellets, rods, and the like.

Although dimensions can vary, typical dimensions can range from about 0.5 mm to about 4 mm width and about 0.2 mm to about 1 mm thickness. Although the total mass of the delivery device can vary, most often the total mass can be from 0.2 mg to 4 mg. For example, about 2 mg total mass can provide effective active agent volume, while also balancing overall size to fit within the target tissue areas.

Figure 6:
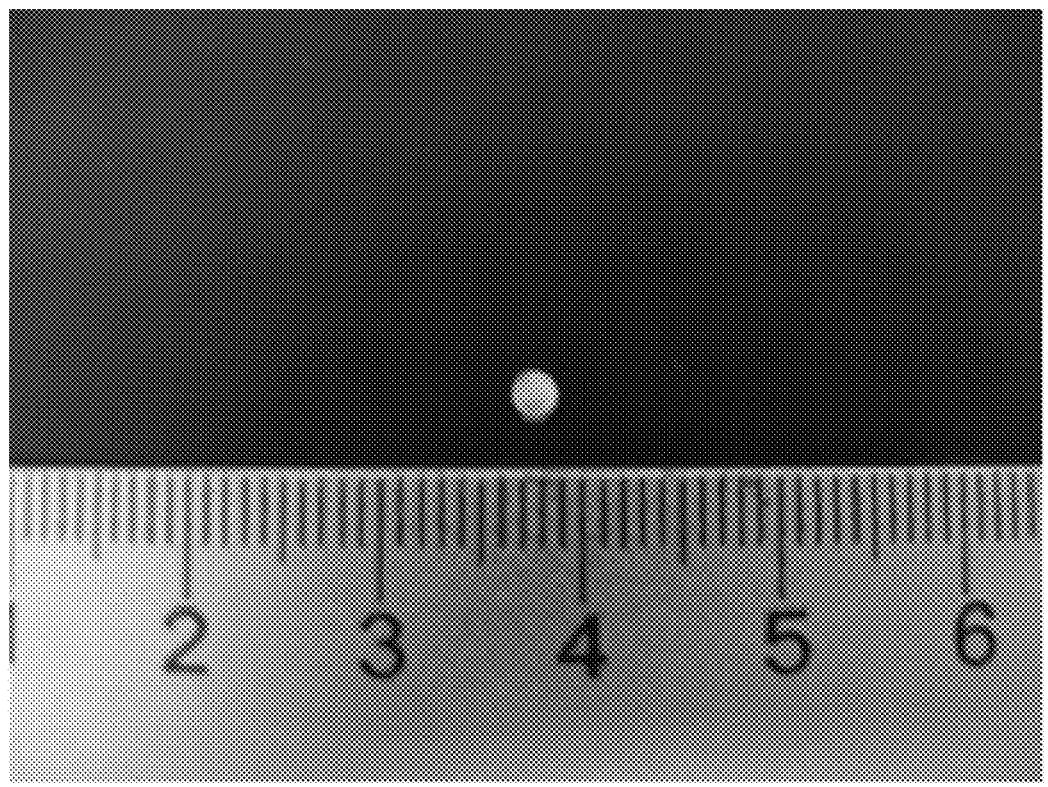
FIG. 6 is a photograph showing bioerodible dexamethasone implant (BDI).

In one alternative embodiment, the device is provided in the form of implants containing the active agent within a biodegradable polymer matrix. The bioerodible polymer may contain one or several excipients depend on the duration of active agent delivery. The implant can be in the following dimensions as shown in FIG. 6, e.g. 2 to 2.5 mm in diameter and 1.0-1.5 mm in thickness. Placement of the implant can be inferior to the intraocular lens (IOL) and implanted during cataract surgery. The implant can be in the shape of round, square shape, crescent or donut shape and depend on the dosage requirement one or two implants can be implanted per eye.

Suitable active agent matrix can include dexamethasone or those listed previously as active agent carriers. Non-limiting examples of active agent matrix materials can include polymeric and non-polymeric materials. Specific non-limiting examples of suitable matrix materials include biodegradable polymers such as PLGA (different ratios of lactic to glycolide content and end groups such as acid or ester termination), PVA, PEG, PLA, PGA, HPMC, hydroxypropylcellulose, sodium carboxymethylcellulose, croscarmellose sodium, polycaprolactone, hyaluronic acid, albumin, sodium chloride block copolymers thereof, and the like. Specific copolymers such as polylactic-polyglycolic acid block copolymers (PLGA), polyglycolic acid-polyvinyl alcohol block copolymers (PGA/PVA), hydroxypropylmethylcellulose (HPMC), polycaprolactone-polyethylene glycol block copolymers, croscarmellose, and the like can be particularly effective. In one aspect, the active agent matrix can be a PLGA having about 45-80% PLA and 55-20% PGA such as about 65% PLA and 35% PGA. In another alternative embodiment, the ratios of PLGA, dexamethasone and Croscarmellose sodium can be 60-90/5-25/5-25 or 50-75/10-40/10-40 ratios.

Figure 4:
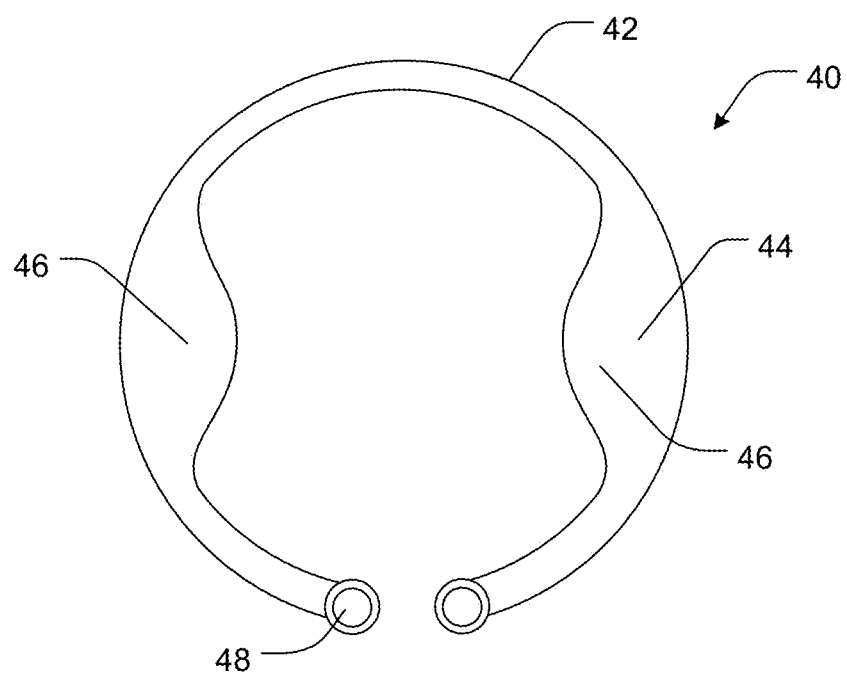
FIG. 4 is a top view of an active agent delivery device having a homogeneous active agent loaded matrix forming the annular body.

FIG. 4 illustrates one configuration for a homogeneous delivery device 40 formed of an active agent matrix and the active agent dispersed therein. In this configuration, the active agent matrix comprises the annular body 42 such that the entire device throughout is formed of the matrix having active agent dispersed therein. In this case, the active agent reservoir 44 extends from external surfaces throughout the interior of the device as active agent is present throughout the matrix. Although the device can generally be initially formed having a complete dosage of active agent dispersed in the device, many matrix materials can also function as a valve which is resealable upon injection of an additional charge of active agent. The configuration shown in FIG. 4 also shows two bulbous portions 46 which provide additional reservoir volume to increase available active agent for a given device size. Other variations in the profile can also be made, as long as the line of sight is preserved. For example, multiple bulbous regions can be distributed along the device arc (e.g. 2, 3, 4 or more). Although typically oriented on inside surfaces of the device arc, such bulbous regions may also be oriented on outside surfaces of the device arc, as long as such features do not interfere with positioning of the device within the capsular bag. Alternatively, the entire ring housing can be made thicker. Optional manipulation handles 48 can also be provided to allow secure handling of the device during implantation or subsequent removal of the device from an eye.

Homogeneous delivery devices can be formed, for example, by mixing a polymer material with a loading amount of active agent to form a matrix dispersion. The loading amount can be chosen to correspond to the desired dosage during diffusion. Loading amount can take into account diffusion characteristics of the polymer and active agent, residual active agent, delivery time, and the like. The matrix dispersion can then be formed into the device shape using any suitable technique. For example, the matrix dispersion can be cast, sprayed and dried, extruded, stamped or the like. Such configurations will most often be formed using a biodegradable matrix, although non-biodegradable materials can also be used. In one alternative formulation, the device can be formed in situ from a suspension of the active agent within a biodegradable polymer matrix precursor. Upon delivery into the target site, the biodegradable polymer matrix precursor can form (via precipitation and/or polymerization) the biodegradable active agent matrix in situ.

With the above homogeneous delivery device, particular efficacy can be provided for treatment of uveitis and postoperative cataract surgery inflammation. For example, dexamethasone can be dispersed within a biodegradable active agent matrix. Although dexamethasone dosage amounts can vary, generally from about 100 mcg to about 400 mcg can be effective for these indications. More specifically, some patients may be categorized as low risk while others can be categorized as high risk due to various factors such as age, secondary complications, pre-existing conditions, etc. Most often, a low risk patient can benefit from a low dosage of about 100 mcg to about 150 mcg. In contrast, a high risk individual can be administered a high dosage of about 250 mcg to about 350 mcg. The BDI-1 implant is specifically designed and tested for the treatment of postoperative surgery inflammation and can deliver pharmaceutical active agent up to 2 weeks. The BDI-2 implant is designed and tested for the treatment of postoperative surgery inflammation and uveitis and can deliver active agent up to 6-8 weeks. Depend on the severity of the inflammation one or two implants can be implanted during surgery per eye.

As previously mentioned, the delivery device herein is targeted for a relatively short delivery duration, and in most cases less than eight weeks. In one alternative, the active agent has a delivery duration of about two weeks to about six weeks. Delivery duration can be a function of the type of polymer used in the matrix, copolymer ratios, and other factors. Although other biodegradable polymers can be suitable such as those listed previously, particularly suitable polymers can include at least one of poly(lactic-co-glycolide), hydroxypropyl methyl cellulose, hydroxyl methyl cellulose, polyglycolide-polyvinyl alcohol, croscarmellose, polycaprolactone, eudragit L100, eudragit RS100, poly(ethylene glycol) 4000, poly(ethylene glycol) 8000 and poly(ethylene glycol) 20,000. The biodegradable active agent matrix can comprise poly(lactic-co-glycolide) having a copolymer ratio from 52/48 to 90/10. In one specific example, the copolymer ratio can be 52-78/48-22 and in another specific example from 60-90/40-10. Although degradation rates can be dependent on such proportions, additional alternative approaches can also be useful such as device coatings, particle encapsulation, and the like.

EXAMPLES

Example 1

A standard clear-corneal phacoemulsification with intraocular lens (Acrysof SA60AT; Alcon) implantation was performed on 35 rabbits. At the time of each surgery, an intraocular device containing an active agent was inserted into a lens capsule of each rabbit. The rabbits were divided into 4 groups, depending on the active agent in the intraocular device. Devices were loaded with 5-15 mg of either Avastin, Timolol, Brimonidine, or Latanoprost. Each group was evaluated to determine the intraocular device and lens stability, capsular fibrosis, and healing of cataract wounds and anterior segment. A subgroup of eyes was evaluated weekly for 4 weeks for inflammation and harvested at 1 month for histopathologic evaluation of capsular and CDR integrity.

Example 2

The surgery and setup as described in Example 1 was repeated, with the exception that aqueous and vitreous taps were performed biweekly and assayed for drug concentrations with HPLC and/or ELISA. In each drug group, half of the eyes were harvested at one month and the other half at two months. This was accomplished as follows: immediately after sacrificing the rabbit and enucleating the eye, the eye was frozen in liquid nitrogen to prevent perturbation and redistribution of drug in eye tissues. The eye was then dissected into 3 parts (aqueous humor, vitreous and retina/choroid layer) to evaluate anatomic toxicity and tissue drug concentration. The intraocular device was retrieved and assessed for remaining drug amounts. The distribution profile of the intraocular device was compared with the conventional intravitreal injection of 2.5 mg/0.1 cc Avastin® for direct comparison of the different delivery methods.

At 2 and 4 months, eyes from the remaining subgroups of rabbits were enucleated, fixed by 10% formalin, embedded in paraffin, step sectioned, stained by hematoxyline and eosin (H & E), and examined for histological changes.

Example 3

Three intraocular devices were implanted into eyes of New Zealand white rabbits under general anesthesia after lens extraction (phacoemulsification technique). Two of the devices were loaded with Avastin and one was loaded with the contrast agent Galbumin as a control. Proper intraocular device position was verified by MRI as well as clinical examination.

Figure 5:
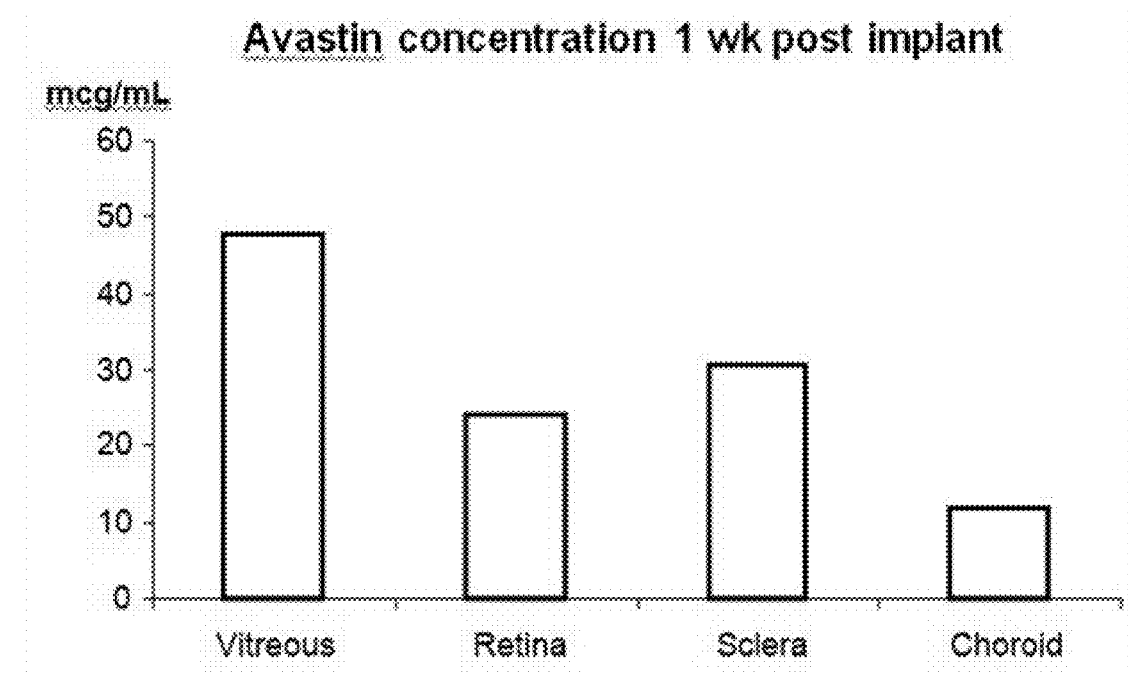
FIG. 5 is a graphical representation of the amount of an active agent present in various eye tissues following implantation of an intraocular device in accordance with a further aspect of the present invention.

The rabbits were sacrificed and the eyes are removed and assayed after 1 week post implantation. Avastin was detected by ELISA in the retina and vitreous at concentrations of 24-48 mcg/mL, and was not present in the control rabbit eye. FIG. 5 shows the amount of Avastin assayed per ocular region at 1 week post implantation.

Example 4

To confirm that placement of implant in the capsular bag and delivers drugs both to the front and back of the eye for short and long term, microparticles were prepared using PLGA [poly(d,l-lactide-co-glycolide), MW. 7000-17000, acid terminated], hydroxypropyl methyl cellulose (HPMC) and dexamethasone. Dexamethasone loaded PLGA microspheres were prepared using standard oil-in-water (o/w) emulsion-solvent extraction method. An amount of 160 mg PLGA was dissolved in 4 mL methylene chloride and 1 mL acetonitrile. An amount of 40 mg dexamethasone and 10 mg of HPMC was dispersed in the PLGA solution by vortexing for 5 min. This organic phase was then emulsified in 20 mL of a 2% (w/v) PVA (MW 90 kDa) solution and homogenized. The resultant emulsion was poured into 200 mL of a 2.0% (w/v) PVA (MW 90 kDa) solution and stirred in an ice bath for 6 min. The contents were stirred for 8 hr at room temperature to evaporate the dichloromethane and acetonitrile to form a turbid microparticulate suspension. The microparticles were separated by centrifugation, washed twice, resuspended in deionized water, and freeze-dried to obtain lyophilized particles. The prepared microparticles were characterized and pelleted using bench top pellet press with 2 mm die set to form an implant.

These implants were sterilized, implanted in the capsular bag of rabbit's eyes. Two dose groups were used (300 and 600 µg), two rabbits were sacrificed from each of low and high dose group at 1, 2, 4, 6 weeks and various tissue samples (aqueous humor, vitreous humor, IOL, iris/ciliary body and retina/choroid) were collected and samples were analyzed by a validated LC/MS/MS method. Microspheres were in the range of 6±2 µM as confirmed by Zetasizer nano and SEM photomicrographs. Drug loading in the microparticles was >99% and the final yield was 60% (i.e. encapsulation efficiency). Drug loading was determined as percent drug loading=(weight of drug loaded/weight of microspheres)×100. Dose related pharmacokinetics with near zero order kinetics was observed in rabbits up to 6 weeks. Further, dexamethasone flow was bidirectional from the endocapsular space into both the anterior and posterior chambers. There were also no cells or formation of fibrin in the anterior and posterior chambers of the eye. Histological examinations revealed all the tissues examined were normal and showed no signs of inflammation.

All the study animals were acquainted to study room conditions once they are out of quarantine and randomized. All the positive control group and implantation groups underwent phacoemulsification and insertion of an intraocular lens (IOL) in both the eyes. Group III and IV received one and two implants per eye respectively.

Group I: Normal control group; n=6

Group II: Phacoemulsification and inserting IOL; DXM drops (up to 4 weeks with tapering) and antibiotic drops (up to 2 days); positive control group; n=6

Group-III: Phacoemulsification and inserting IOL; BDI implant low dose (one implant per eye) and antibiotic drops up to 2 days (b.i.d.) after surgery; n=8

Group-IV: Phacoemulsification and inserting IOL; BDI implant high dose (two implants per eye) and antibiotic drops up to 2 days (b.i.d.) after surgery, n=8

Results of in vitro release kinetics were determined. All the batches exhibited biphasic release pattern with initial burst release on day-1 and thereafter slow and sustained release. The burst effect was slightly higher with implants containing HPMC.

A total of 16 animals (32 eyes) received the implant. Dexamethasone concentrations are presented in FIG. 10 through FIG. 13. The implants degraded slowly over 4 weeks and by week 6 were completely disappeared. Therapeutic concentrations of DXM was found up to week 6 with minimal systemic exposure (<40 ng/mL with high dose), whereas, with dexamethasone drops systemic exposure was higher (>150 ng/mL during week 1). Mean PK parameters for BDI-2 implant and positive control group in aqueous humor, vitreous humor, retina/choroid, and iris/ciliary body are shown in Table 1 and 2.

removing the residual solvent by drying the product under high vacuum for 3 days. Various implants were prepared using PLGA [poly(d,l-lactide-co-glycolide), MW. 7000-17000, acid terminated], hydroxypropyl methyl cellulose (HPMC), croscarmellose sodium (cross linked sodium carboxymethylcellulose), hydroxypropyl cellulose and dexamethasone in several different compositions.

The dried particles were directly pelleted using bench top pellet press with a 2 mm die set to form an implant.

The selected BDI-1 implants (from in-vitro release studies, FIG. 7) were sterilized, implanted in the capsular bag of rabbit's eyes. Two implants with different composition and dose were tested in-vivo in NZW rabbits to establish pharmacokinetics. Two rabbits were sacrificed at 2, 6, 10, 15 days and various tissue samples (aqueous humor, vitreous humor, IOL, iris/ciliary body and retina/choroid) were collected and samples were analyzed by a validated LC/MS/MS method. Pharmacokinetics with near zero order kinetics was observed in rabbits up to 15 days. Further, dexamethasone flow was bidirectional from the endocapsular space into both the anterior and posterior chambers. There were also no cells or formation of fibrin in the anterior and posterior chambers of the eye. Histological examinations revealed all the tissues examined were normal and showed no signs of inflammation.

TABLE 1

Pharmacokinetics in aqueous humor and vitreous humor

| Parameter | Low dose: 300 µg | | High dose: 600 µg | | Dexamethasone Drops | |
|---|---|---|---|---|---|---|
| | Aqueous humor | Vitreous humor | Aqueous humor | Vitreous humor | Aqueous humor | Vitreous humor |
| $C_{max}$ (ng/mL) | 650 ± 109 | 892 ± 151 | 1570 ± 113 | 1379 ± 233 | 62 ± 24 | 3 ± 0 |
| $T_{max}$ (day) | 19 ± 8 | 28 ± 0 | 7 ± 0 | 28 ± 0 | 14 ± 0 | 16 ± 11 |
| $AUC_{0-t}$ (day*ng/mL) | 15231 ± 361 | 18317 ± 2435 | 28202 ± 3369 | 32933 ± 4027 | 1023 ± 320 | 61 ± 5 |
| $C_{last}$ (ng/mL) | 8 ± 3 | 2 ± 1 | 52 ± 18 | 85 ± 23 | 6 ± 2 | 2 ± 1 |

TABLE 2

Pharmacokinetics in retina/choroid and iris/ciliary body

| Parameter | Low dose: 300 µg | | High dose: 600 µg | | Dexamethasone Drops | |
|---|---|---|---|---|---|---|
| | Retina/Choroid | Iris/CB | Retina/Choroid | Iris/CB | Retina/Choroid | Iris/CB |
| $C_{max}$ (µM) | 21 ± 4 | 35 ± 5 | 117 ± 40 | 209 ± 24 | 3 ± 1 | 3 ± 2 |
| $T_{max}$ (day) | 14 ± 0 | 7 ± 0 | 23 ± 8 | 14 ± 0 | 14 ± 0 | 9 ± 4 |
| $AUC_{0-t}$ (day*µM) | 455 ± 61 | 759 ± 132 | 2226 ± 1105 | 3913 ± 685 | 48 ± 16 | 42 ± 27 |
| $C_{last}$ (µM) | 1.3 ± 0.6 | 1.5 ± 0.5 | 12 ± 8 | 13 ± 10 | 0.2 ± 0.1 | 0.5 ± 0.3 |

Intraocular pressure was normal in all the groups. Further, there were no signs of anterior or posterior chamber inflammation as assessed with Slit lamp biomicroscopy and confirmed by histological examination. There was a trend in increase in retinal thickness in animals treated with dexamethasone drops whereas, implants maintained retinal thickness.

The PLGA polymer degrades in to lactic and glycolic acid through hydrolysis, then further degrades in to carbon dioxide and water before eliminating from the body. Implants did not migrate to the center to obstruct the visual field.

Figure 7:
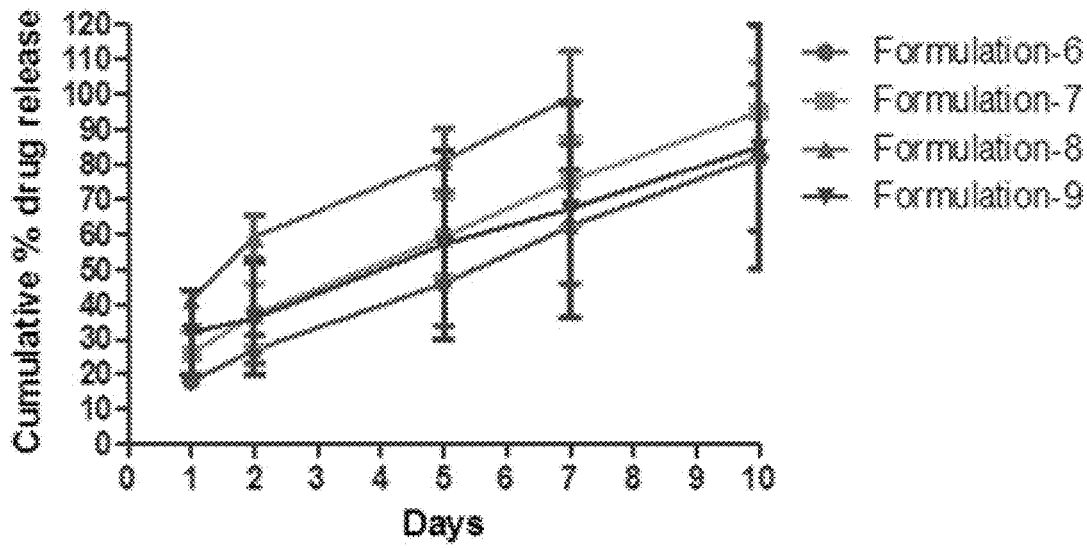
FIG. 7 is a graph of in-vitro release kinetics of the BDI-1 implant. Data are presented as mean±SD (n=3).

BDI-1 implant was manufactured by following partial solvent casting method with subsequent evaporation and Results of in vitro release kinetics are presented in FIG. 7. All the batches exhibited smooth release pattern with initial burst release on day-1 and thereafter slow and sustained release. The burst effect was slightly higher with implants containing HPMC.

Figure 8:
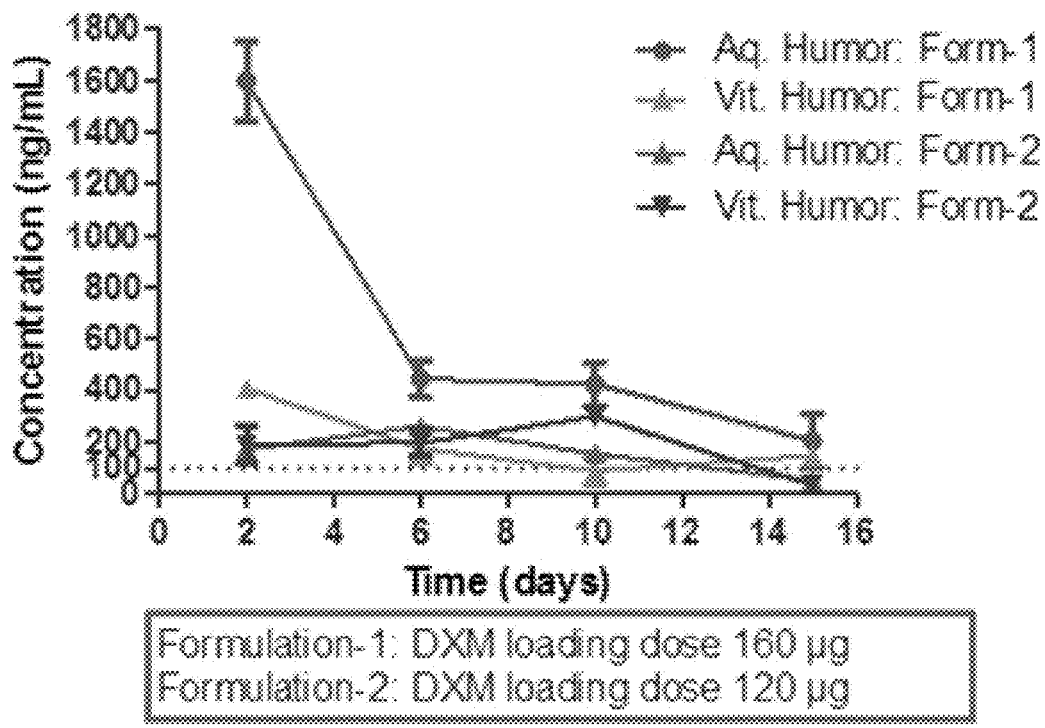
FIG. 8 time vs concentration profile of BDI-1 implant with 120 to 160 µg of dexamethasone (DXM) in aqueous and vitreous humor of New Zealand White (NZW) rabbits.
Figure 9:
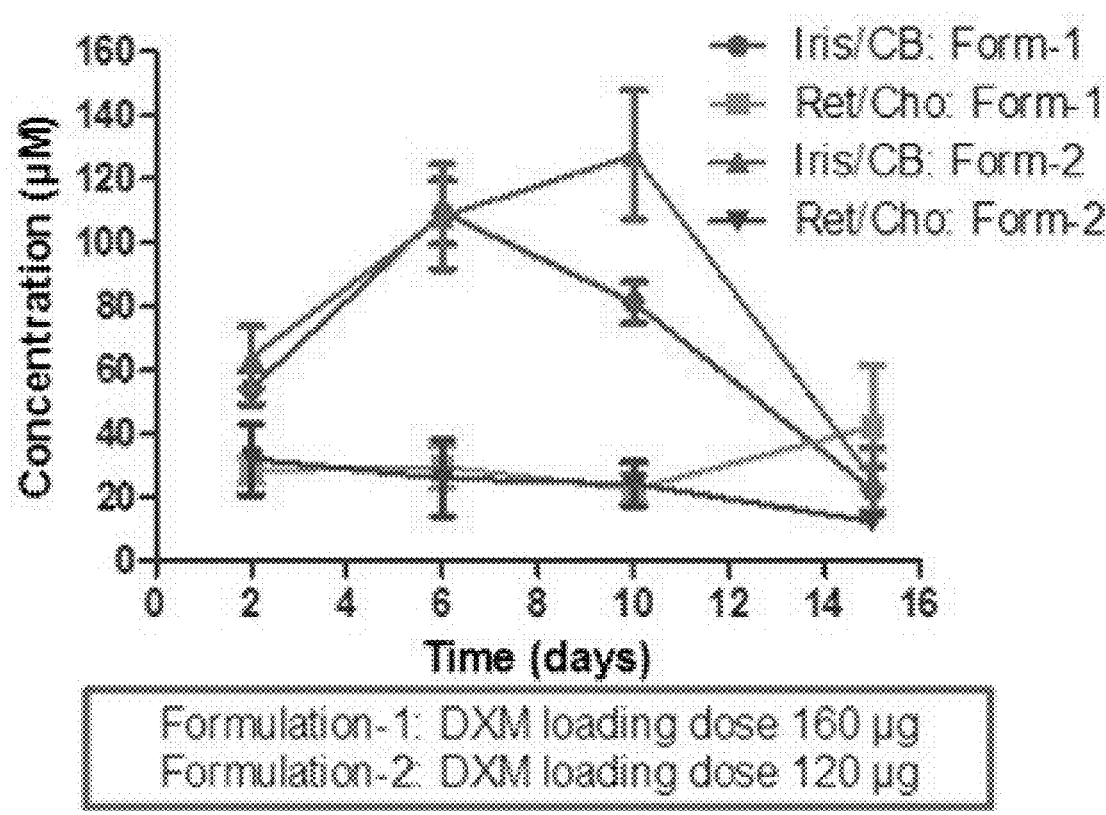
FIG. 9 time vs concentration profile of BDI-1 implant with 120 to 160 µg of DXM in iris/ciliary body and retina/choroid of NZW rabbits.
Figure 10:
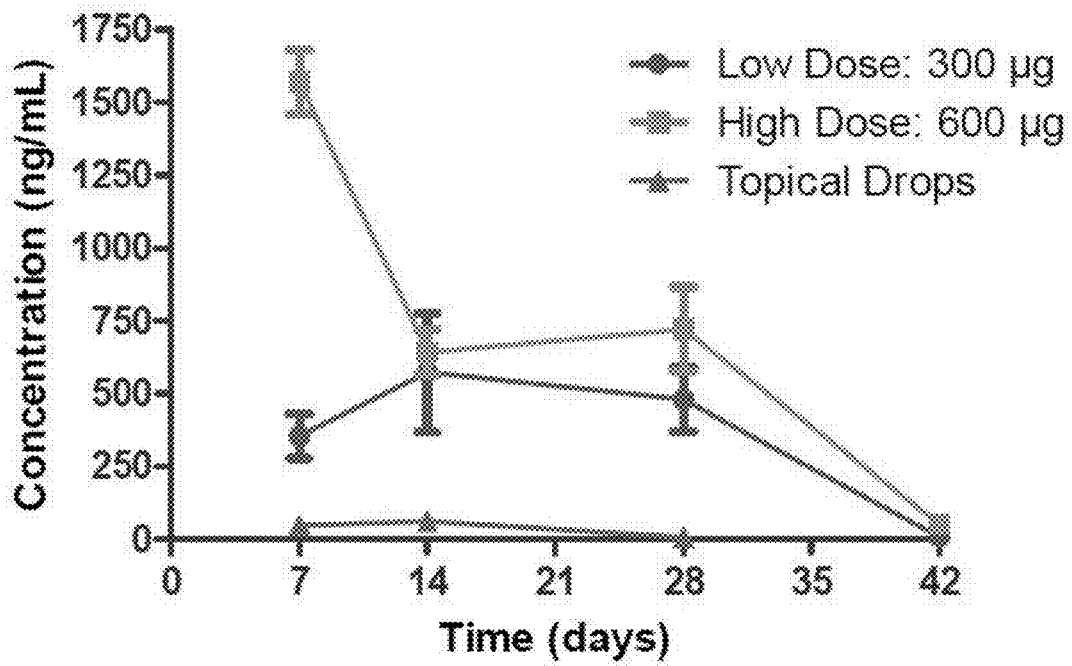
FIG. 10 is a graph of time vs. concentration profile of BDI-2 implant and topical drops in aqueous humor of New Zealand white rabbits.
Figure 11:
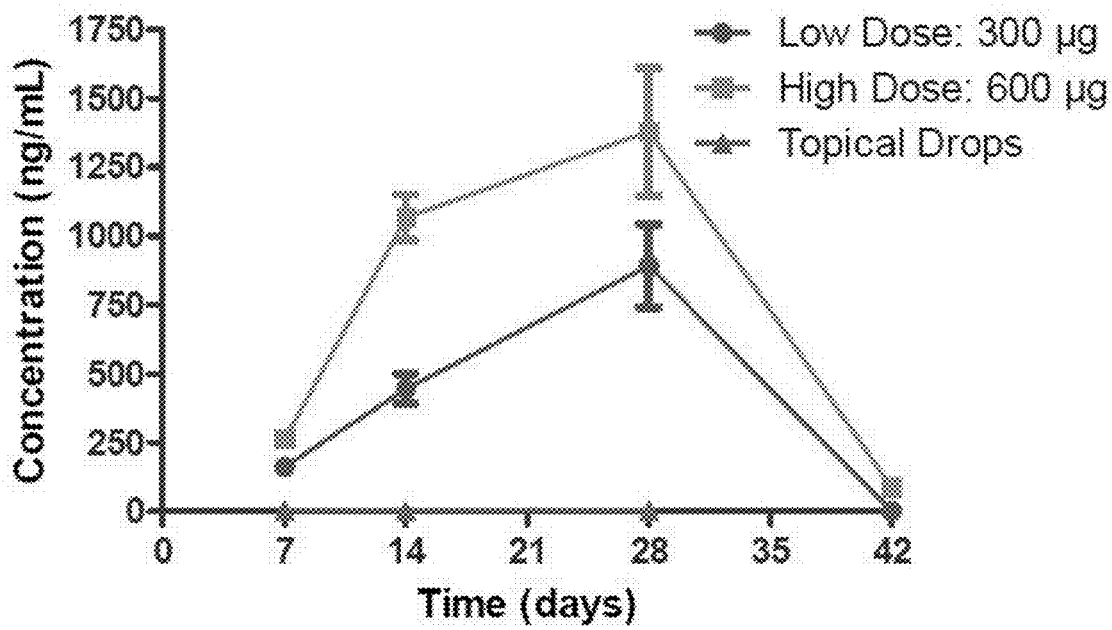
FIG. 11 is a graph of time vs. concentration profile of BDI-2 implant and topical drops in vitreous humor of New Zealand white rabbits.
Figure 12:
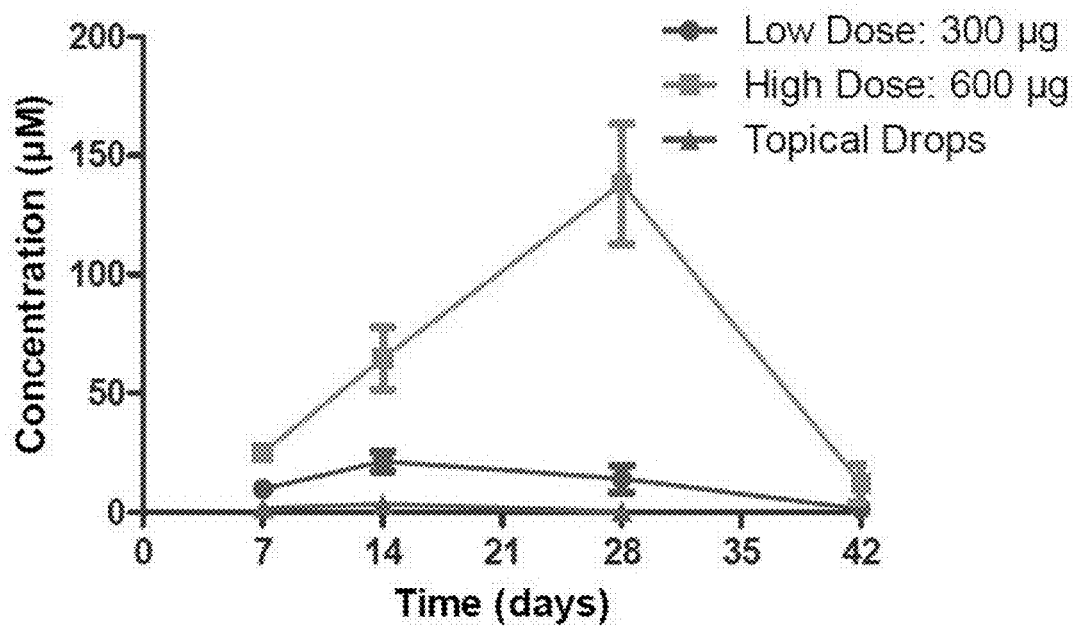
FIG. 12 is a graph of time vs. concentration profile of BDI-2 implant and topical drops in retina/choroid of New Zealand white rabbits.
Figure 13:
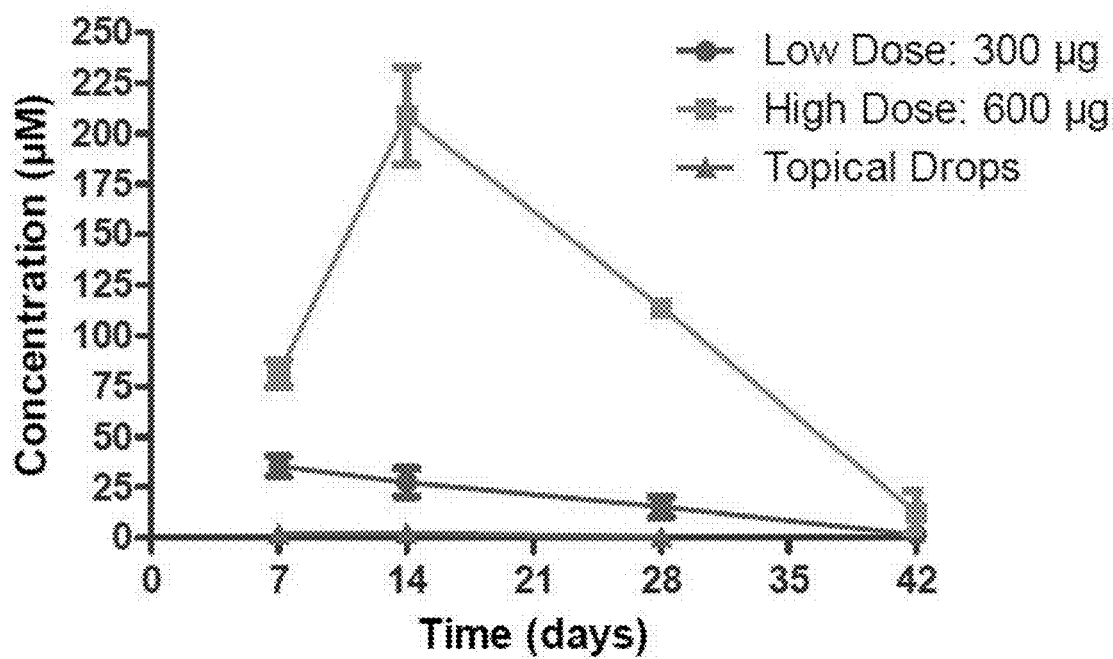
FIG. 13 is a graph of time vs. concentration profile of BDI-2 implant and topical drops in iris/ciliary body of New Zealand white rabbits.

A total of 8 animals (16 eyes) received the implant containing 120 µg of DXM. DXM concentrations are presented in FIG. 8 FIG. 9. The implants eroded slowly over 10 days and reaching trough concentrations of DXM by day 15. The implants are degraded by 80% of its mass by day 15 and expected to fully degrade by day 20. Therapeutic concentrations of DXM was found up to day 15 with minimal systemic exposure (<23 ng/mL), whereas, with dexamethasone drops systemic exposure was higher (>150 ng/mL during week 1, in-house data).

It should be understood that the above-described arrangements are only illustrative of application of the principles of the present invention. Numerous modifications and alternative arrangements may be devised by those skilled in the art without departing from the spirit and scope of the present invention. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of treating an eye condition, comprising administering an active agent to the eye using an intraocular active agent delivery device by inserting the delivery device into a lens capsule or ciliary sulcus of the eye, wherein the eye condition is at least one of post-operative cataract surgical inflammation and uveitis and the intraocular active agent delivery device comprises an active agent dispersed within a biodegradable active agent matrix, said active agent including dexamethasone and said delivery device being configured to fit within a lens capsule or ciliary sulcus of an eye, wherein the delivery device is a homogeneous device formed of the active agent and the biodegradable active agent matrix.

2. The method of claim 1, wherein the inserting is performed during a cataract surgery.

3. The method of claim 1, wherein the inserting is performed after a cataract surgery to treat the post-operative cataract surgical inflammation.

4. The method of claim 1, wherein the eye condition is uveitis.

5. The method of claim 1, wherein the delivery device is in the form of a suspension of the active agent within a biodegradable polymer matrix precursor, and the inserting includes injecting the suspension into the lens capsule or ciliary sulcus such that the biodegradable polymer matrix precursor forms the biodegradable active agent matrix in situ.

6. The method of claim 1, wherein the delivery device has a width of 0.5 to 4 mm and a thickness from 0.2 to 1.5 mm.

7. The method of claim 1, wherein the delivery device is shaped as a disc having a diameter of 2 to 2.5 mm and a thickness of 0.2 to 1.5 mm.

8. The method of claim 1, wherein the biodegradable active agent matrix comprises poly(lactic-co-glycolide) and the delivery device further includes croscarmellose in the active agent matrix.

9. The method of claim 1, wherein the active agent has a delivery duration of about two weeks to about 6 weeks, and can deliver drug to both the anterior and posterior segments of the eye.

10. The method of claim 1, wherein the biodegradable active agent matrix comprises at least one of poly(lactic-co-glycolide), polylactic-polyglycolic acid block copolymers (PLGA), hydroxypropyl methyl cellulose, hydroxyl methyl cellulose, polyglycolide-polyvinyl alcohol, croscarmellose sodium, hydroxypropylcellulose, sodium carboxymethylcellulose, polyglycolic acid-polyvinyl alcohol block copolymers (PGA/PVA), hydroxypropylmethylcellulose (HPMC), and polycaprolactonepolyethylene glycol block copolymers.

11. The method of claim 1, wherein the biodegradable active agent matrix comprises poly(lactic-co-glycolide) having a copolymer ratio from 52/48 to 90/10.

12. The method of claim 1, wherein the delivery device is shaped as a disc or pellet.

13. The method of claim 1, wherein the delivery device has a total mass of 0.2 mg to 4 mg.

* * * * *